United States Patent
Wells

(10) Patent No.: US 6,728,592 B2
(45) Date of Patent: Apr. 27, 2004

(54) STREAK DETECTION IN PAPERMAKING

(75) Inventor: Charles H. Wells, Redwood City, CA (US)

(73) Assignee: Voith Paper Automation, Inc., Los Gatos, CA (US)

(*) Notice: Subject to any disclaimer, the term of this patent is extended or adjusted under 35 U.S.C. 154(b) by 135 days.

(21) Appl. No.: 09/935,375

(22) Filed: Aug. 22, 2001

(65) Prior Publication Data

US 2002/0104635 A1 Aug. 8, 2002

Related U.S. Application Data

(63) Continuation-in-part of application No. 09/645,780, filed on Aug. 24, 2000, now abandoned.

(51) Int. Cl.$^7$ .............................................. G06F 19/00
(52) U.S. Cl. ....................... 700/122; 700/129; 162/198; 162/252
(58) Field of Search ................................ 700/127–129, 700/154–156, 122; 356/429–431; 250/559.03, 559.39, 559.24, 559.06, 559.45, 559.46; 73/59; 702/81; 162/198, 252, 262

(56) References Cited

U.S. PATENT DOCUMENTS

| | | | | |
|---|---|---|---|---|
| 3,612,839 A | * | 10/1971 | DeWitt et al. ................. 702/81 |
| 3,914,585 A | * | 10/1975 | Wilhelm et al. ............. 700/129 |
| 4,000,402 A | * | 12/1976 | Higham ....................... 700/129 |
| 4,950,911 A | | 8/1990 | Williams et al. ............ 250/563 |
| 5,196,715 A | | 3/1993 | Burk et al. .................. 250/562 |
| 5,696,591 A | * | 12/1997 | Bilhorn et al. .............. 356/429 |
| 5,949,550 A | | 9/1999 | Arndt et al. ................. 356/430 |

* cited by examiner

Primary Examiner—Leo Picard
Assistant Examiner—Steven R. Garland
(74) Attorney, Agent, or Firm—Coudert Brothers LLP

(57) ABSTRACT

A method of detecting streaks in a web of, for example, moving paper which may be moisture, basis weight or caliper. A cross-direction profile is sensed and a moving average computed and then using minimum thresholds for the variation of the streak value from the average and its width in profile data boxes, the streak is detected.

5 Claims, 5 Drawing Sheets

STREAK DETECTION IN PAPERMAKING

CROSS REFERENCE TO RELATED APPLICATION

This is a continuation in part application of Ser. No. 09/645,780, filed Aug. 24, 2000 and now abandoned.

FIELD OF THE INVENTION

The present invention is directed to a method of streak detection in papermaking and more specifically to a method which is automatically done by computer techniques.

BACKGROUND OF THE INVENTION

Computer control systems are well known for monitoring the characteristics of a moving sheet of paper, such characteristics including moisture, basis weight, and caliper, and using this monitored information to control what are known as actuators, to control the parameter to a desired set point. Even with such control, anomalies in the machine direction, that is the direction of the moving sheet or web, may occur. These are known as streaks and such streaks can and are seen on a visual display unit which has been color coded in conjunction with present day computer control systems. Such a display may be used by an operator to tune or correct an actuator. After the operator views several of the streaks, however, the control action is very subjective. In addition, the true magnitude of a streak is obscured by noise and there may be many minor anomalies of no consequence thus obscuring the overall control picture.

OBJECT AND SUMMARY OF INVENTION

It is therefore a general object of the present invention to provide for an automatic method of detecting streaks.

In accordance with the above object, there is provided a method of detecting streaks, anomalies of a parameter of a web in a machine direction, in a machine producing a moving web which moves in a machine direction, having a plurality of actuators in a cross-direction to the machine direction for controlling a predetermined parameter and having a scanner moving across said web of sheet material in a cross-direction, the scanner measuring in a cross or profile direction a predetermined parameter of the web, to thereby detect data relating to said streaks, with a plurality of data boxes, each data box containing data as to a parameter at an instant of time for each of a plurality of said profiles. The method comprising the following steps of computing the moving average of the data detected in x number of profiles, for example, 10 profiles, and determining an average of the data box data.

A height, H, is chosen which is a number related to the value of the predetermined parameter, which is dependent on the quality and use of the web which is the maximum allowed deviation from the average.

Residuals, $R_i$, are computed from the average and checking for the absolute values of $R_i$ greater than H by counting consecutive data boxes with a parameter value greater than H, where i is 1–N, where N is equal to the number of data boxes in a profile.

A value, W, is chosen depending on quality and use of the web, which is a number equal to the consecutive number of data boxes to define a streak.

If the count of consecutive data boxes is equal or greater than W, the profile location of the streak is stored, namely its location along the machine direction and along the profile of the web for use in correction of the actuator to minimize such streak.

DETAILED DESCRIPTION OF PREFERRED EMBODIMENT

Figure 1:
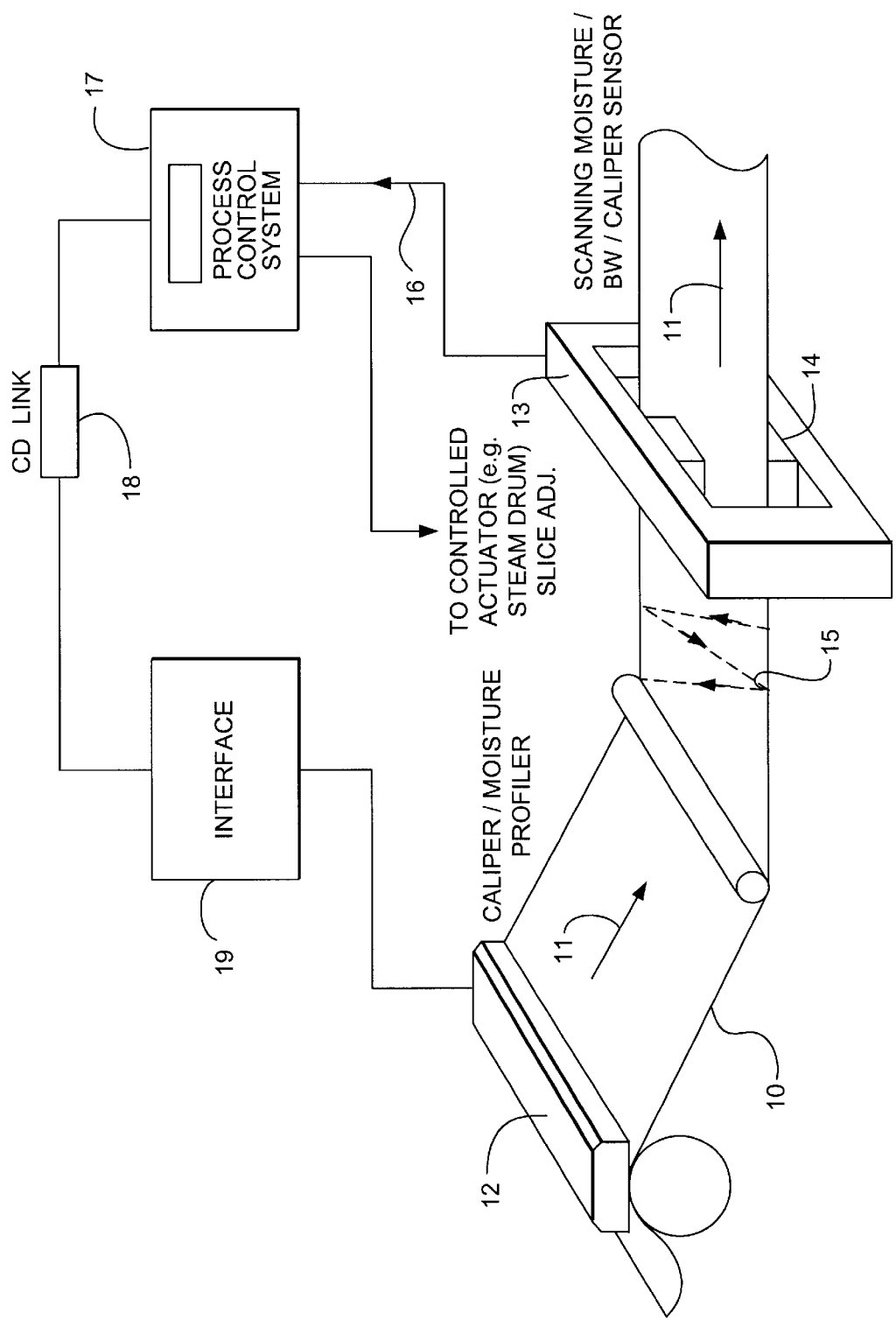
FIG. 1 is a block diagram showing the overall system in which the present invention is used.

The papermaking control system illustrated in FIG. 1 can control various parameters of the paper such as moisture, basis weight or caliper and this occurs on various slices or zones on the paper 10 being manufactured by a paper machine which is moving in a machine direction indicated by the arrows 11. A typical technique of measuring a parameter such as moisture, basis weight or caliper is by a scanning sensor 13 which scans in a cross-direction by the use of a pair of scanning heads 14 which, for example, every 30 seconds scan across the paper and then make a turn-around and scan in the opposite direction to form a zig-zag pattern of scans down the length of the paper shown at 15. The outputs of the scanner 13 are on line 16 and go to a process control system 17 to drive a upstream caliper/moisture or other type of profiler 12 through an interface unit 19 and a CD link 18. In addition, the output of the process control system may also control steam drum actuators or slice adjustments of the head box. All of these may affect the quality in the cross-direction or the profile of the paper and produce streaks depending on the tuning of the particular actuator device.

Figure 2:
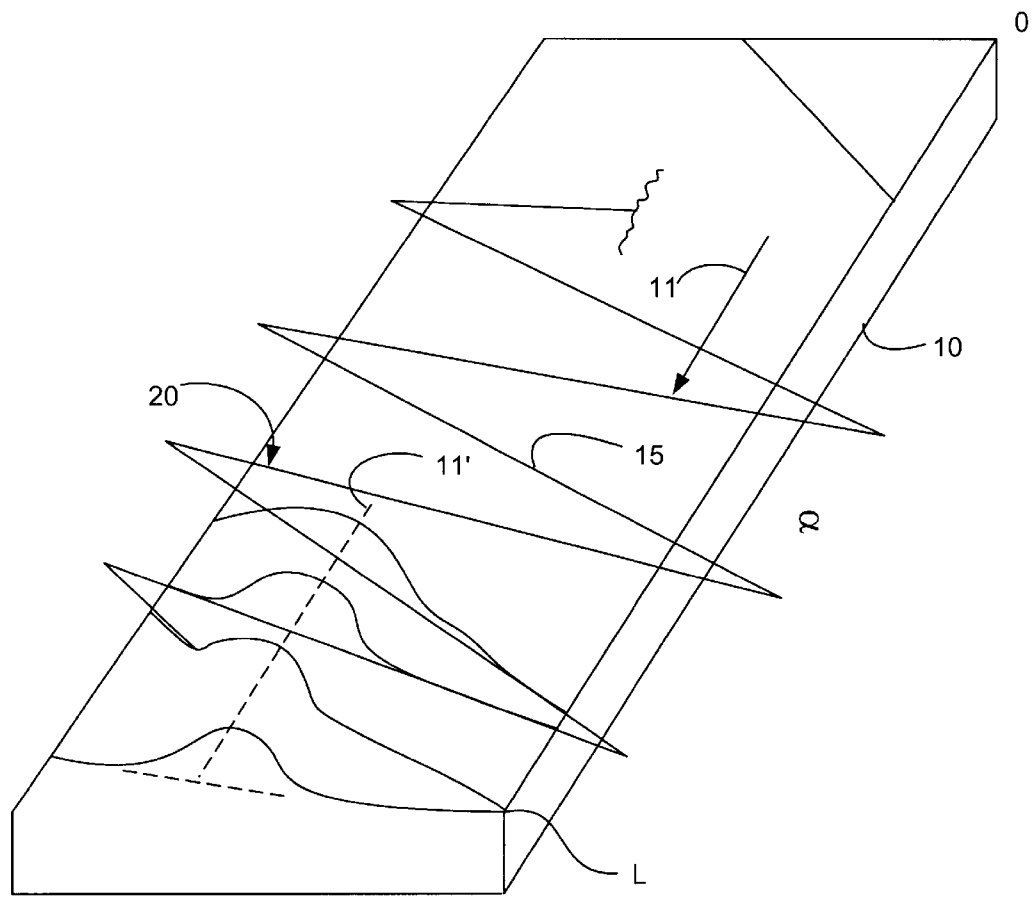
FIG. 2 is a perspective view illustrating a streak on a moving web.

FIG. 2 illustrates a particular length of paper 10 moving in direction 11 which is of length, L. This length may be predetermined such as, for example, the length of paper occurring for 10 scans 15 (see also FIG. 1) across the paper. If the paper is moving at normal speed, this could be 3,000 feet of paper. An anomaly in the paper or streak 20 is illustrated which occurs along a moving line 11'. In the case of caliper, there might actually be a physical bulge or depression in the paper. However, in the case of moisture or basis weight, the symbolic curves 20 merely indicate an increase or decrease from the set point or average value of the paper. And, of course, each of the curves 20 occurs along a particular scan or profile. Of course the number of scans, W1, in the machine direction, MD, is one of the criteria for streak detection and is chosen based on many factors. A general one is the quality specification of that particular papermaking machine. Another is on the paper converter's final use. For example food boxes may not tolerate streaks longer than 3 scans. W1 would be set for that amount.

Figure 3:
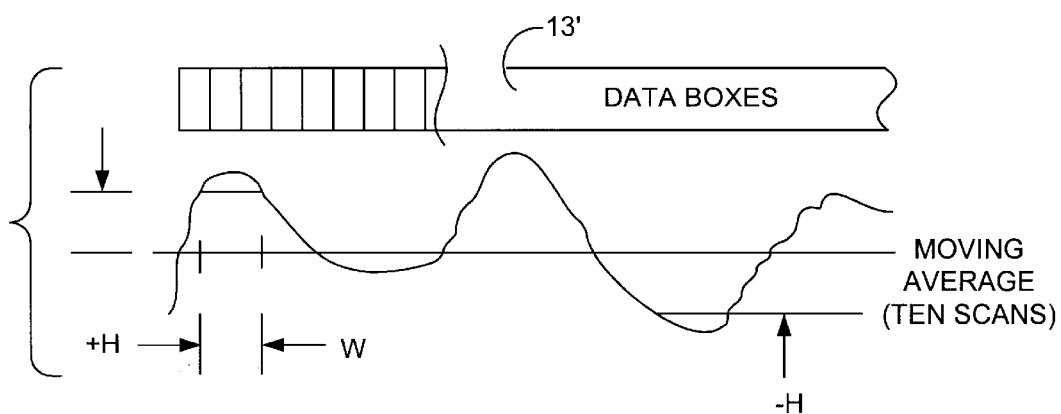
FIG. 3 is an idealized waveform illustrating a profile used in the present invention.

FIG. 3 illustrates an idealized scan in the cross-direction of a parameter of the paper which as discussed above may be basis weight, caliper or moisture. This profile scan of FIG. 3 represents the moving average of the data detected in x number of profiles or scans, for example, 10 scans, which, as discussed above, might represent 3,000 feet of paper. When the average is taken, the values greater than a selected value, H, are determined to be values that would be unacceptable from a quality control point of view. This in turn is dependent on the particular commercial use to which the final manufactured paper is to be put. Specifically, for example, for newsprint excessive moisture might cause smudging of ink, etc. The curve of FIG. 3 is derived from the scanning sensor 13 which, as it scans across the paper, sequentially acquires consecutive data labeled data boxes 13'. As will be discussed below, if a streak or abnormality in the paper occurs over more than, for example, three to six consecutive data boxes then it is considered a significant anomaly so that a correction or returning of an actuator should be made. Again, the selection of W or H is made by the operator and is dependent on the quality of the paper desired and the use to which it is put commercially. As discussed above, the curve of FIG. 3 is very idealized and noise spikes may occur so that if this curve were to be observed visually it would be very difficult to interpret.

Figure 4:
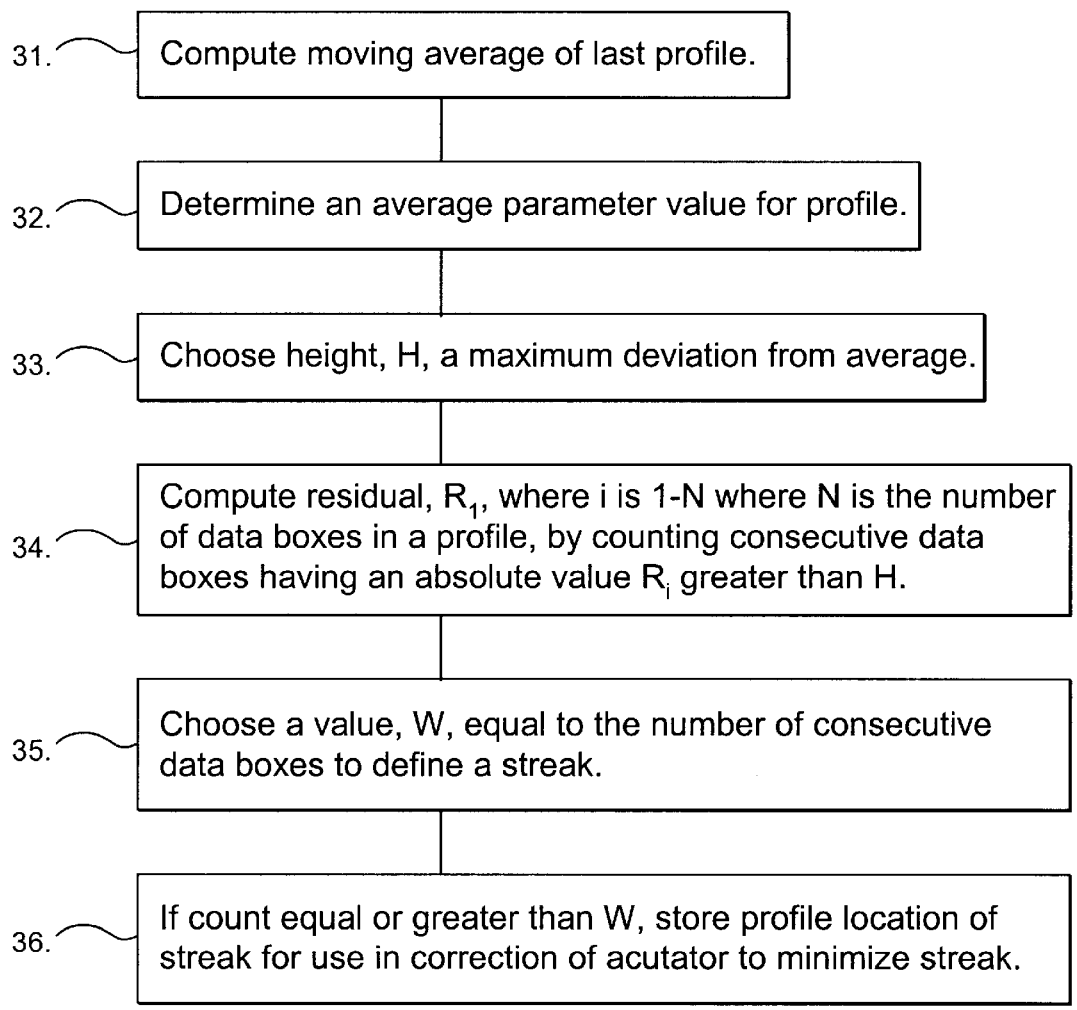
FIG. 4 is a flow chart embodying the present invention.

FIG. 4 illustrates the computing technique accomplished in the process control system 17 where the location and detection of streaks representing a significant anomaly (that is, an anomaly which is susceptible to correction of the actuator) may be detected. In step 31, the moving average profile of the data detected in x number of previous profiles is computed, for example, 10 profiles. A typical moving average profile curve is illustrated in FIG. 3. Then, by standard mathematical techniques in step 32, the moving average is determined using this profile. In step 33, a height, H, is chosen which is a number related to a maximum deviation from the average which is permitted, or, in other words, is a maximum allowed deviation which, when exceeded, is indicative that a control correction should be made. The height of a streak is normally defined in sensor units. As illustrated in FIG. 3, negative and positive values of H can be above or below the average value. A typical visible streak would be at least one sigma above or below the average. Next, in step 34, a residual, $R_i$, from the average is computed where i is from 1 to N where N is the number of data boxes in a profile; that is, data boxes 13' of FIG. 3. Because negative or positive values can occur, the absolute values of $R_i$, are checked. Then, those greater than H are consecutive data boxes that are counted. Of course, as discussed above, consecutive data boxes are counted in order to ensure that interfering noise is not included. In order to implement the above as shown in step 35, a value, W, (see FIG. 3) is chosen which is equal to the number of consecutive data boxes which defines a streak which must be corrected. Again, this depends on the quality desired and the ultimate use of the web. Finally, in step 36, if the count of consecutive data boxes is equal or greater than the chosen W, the profile location, namely the location along the machine direction and along the profile, which is normally a databox number on the centerline of the streak, is stored for use in correction of the actuator to minimize the streak.

Thus the classification of the streak may be by its height, H, its machine direction length, W1, or the number of consecutive cross direction data boxes, W. And any one of these parameters may be chosen to define a criterion for an unwanted streak; by themselves or in combination.

Actuator operation to eliminate streaks may take many forms. Where the parameter is moisture and a streak of excess moisture is present, more energy in the form of heat can be added to eliminate it. For caliper or thickness which is excessive, heat can be used with a calendar roll to reduce caliper. Diagonal streaks and their causes are more complicated; there may be hydraulic problems in the headbox such as dilution problems or obstructions. Also felt on wire problems may exist. For all of these streak problems an alarm may be actuated to alert the operator (or via the internet send an appropriate e-mail).

Figure 5:
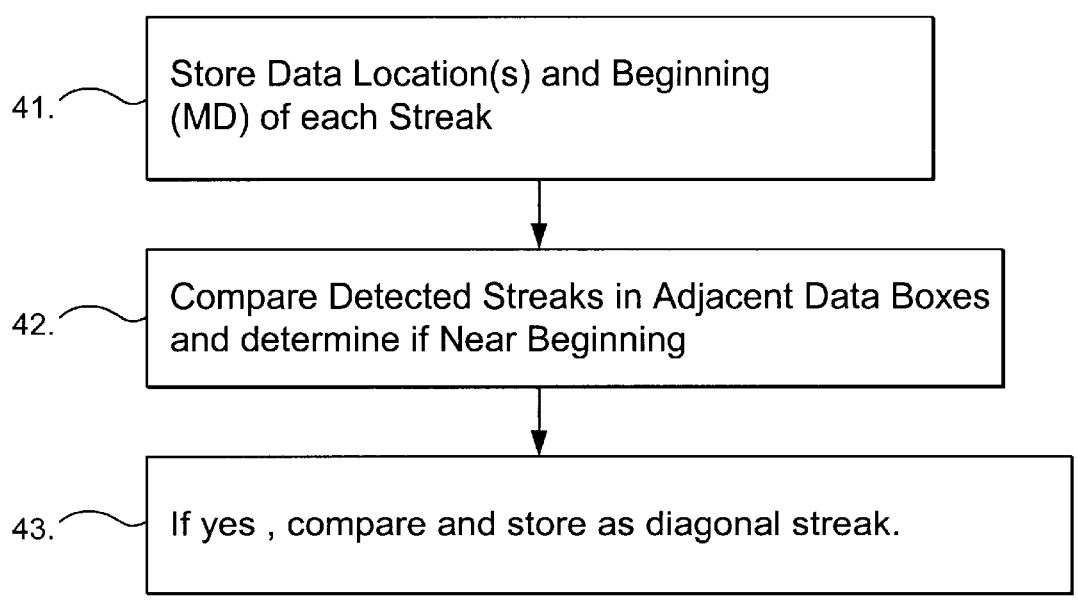
FIG. 5 is a flow chart of another embodiment of the invention.
Figure 6:
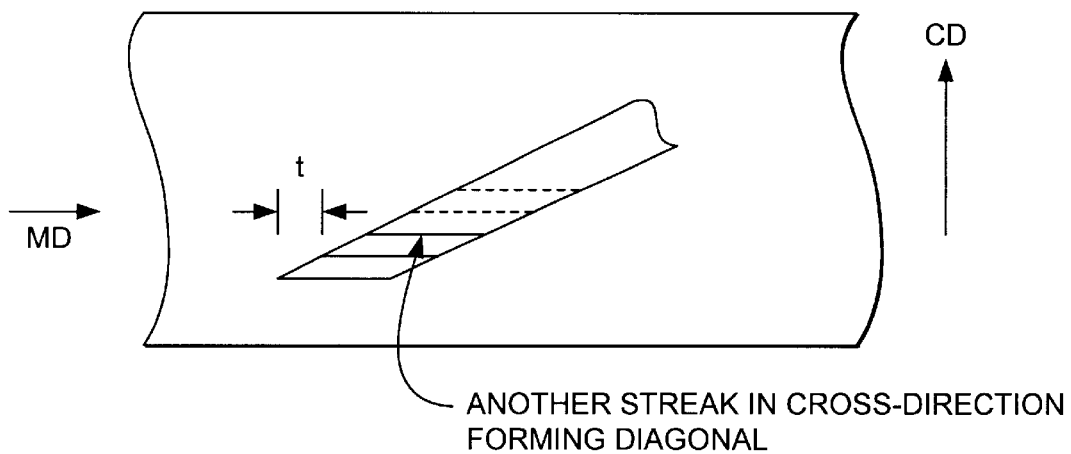
FIG. 6 is a top view of a web illustrating a diagonal streak.

To detect streaks of the diagonal type the steps illustrated in FIG. 5 are used in step 41 data box locations are stored and the beginning (in time in the machine direction, MD) of each detected streak. In step 42 detected streaks are compared in adjacent or nearby data boxes and it is determined whether or not their beginnings are near the beginning of the first streak. If yes, in step 43 this data is compiled and stored as a diagonal streak. FIG. 6 shows the foregoing and the close relationship in time, t, of adjacent streaks.

Figure 7A:
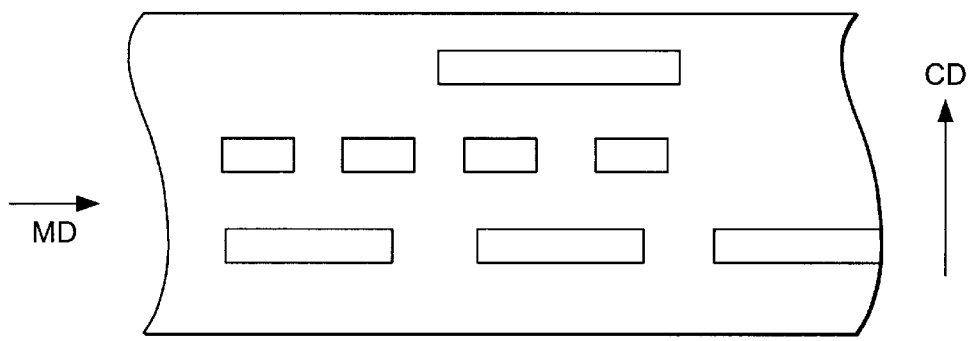
FIG. 7A is a top view of a web showing multiple streaks.
Figure 7B:
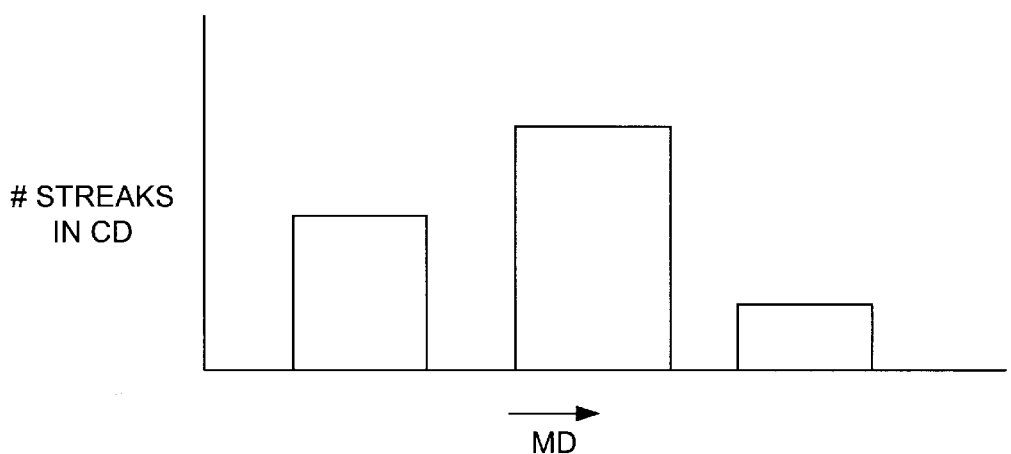
FIG. 7B is a histogram of FIG. 7A.

Detected streaks may also yield other information by the use of a histogram. In FIG. 7B, the number of streaks in the cross direction ("CD") vs machine direction illustrates how streaks are repeating in the MD. FIG. 7A is the raw data from which FIG. 7B was constructed.

FIG. 7 also illustrates how the characteristics of streak displays may be matched to found problems in the headbox, felt, or wire. For example a repeated streak if it occurs every three hours may be due to some action by an operator. On the other hand fast cyclic streaks might indicate a felt or roll problem; or perhaps the whitewater recovery level controller is not working properly. Such fast cycles may also be detected or analyzed by Fourier Transform techniques.

Thus, an effective technique has been provided to automatically detect streaks for which an actuator correction should be made.

What is claimed is:

1. In a machine for producing a moving web of sheet material in a machine direction, said machine including at least one actuator for controlling a parameter of said web and including a scanner that moves across said web in a cross direction to said machine direction, said scanner for measuring a plurality of discrete data points (data boxes) along said cross direction, each pass of said scanner across said web defining a profile of said data boxes, a method of detecting streaks in said web that represents an anomaly in said parameter comprising the steps of:

computing the moving average of the data detected in a predetermined number of profiles;

determining an average based on said data box data;

choosing a height, H, which is a number related to a value of said parameter, where H is a predetermined maximum allowed deviation from said average;

computing residuals, Ri, from the average and checking for the absolute values of Ri greater than H by counting consecutive data boxes with a parameter value greater than H, where i is 1–N, where N is equal to the number of data boxes in a profile;

choosing a value, W, depending on quality and use of the web, which is a number equal to the consecutive number of data boxes to define a streak; and if W consecutive values of $R_i$ exceed said threshold H, storing a profile location of said streak, wherein said profile location is a location of said streak along said machine direction and along said profile cross direction of said web for use in correction of said at least one actuator to minimize such streak.

2. A method of detecting streaks as in claim 1 where diagonal streaks are detected and including the steps of determining if a streak is detected in adjacent groups of data boxes if said streaks are detected and spatially near each other in said machine direction.

3. A method of detecting streaks as in claim 1 including the steps of storing detected streaks with regard to repetition in said machine direction and forming a histogram showing a number of streaks in said cross direction versus said machine direction.

4. A method of claim 1, wherein $R_i$ is a function of both said moving average and said average based on said data box data.

5. In a machine for producing a moving web of sheet material in a machine direction, said machine including at least one actuator for controlling a parameter of said web and including a scanner that moves across said web in a cross direction to said machine direction, said scanner for measuring a plurality of discrete data points (data boxes) along said cross direction, each pass of said scanner across said web defining a profile of said data boxes, a method of detecting streaks in said web that represents an anomaly in said parameter comprising the steps of:

computing the moving average profile of the data detected in a predetermined number of profiles wherein W1 is the number of profiles to average in the moving average;

determining an average based on said data box data;

choosing a height, H, which is a number related to a value of said parameter, where H is a predetermined maximum allowed deviation from said average and is dependent on the quality and use of said web;

computing residuals, Ri, from the average and checking for the absolute values of Ri greater than H by counting consecutive data boxes with a parameter value greater than H, where i is 1–N, where N is equal to the number of data boxes in a profile;

defining a streak by at least one of the following criteria:
    a) choosing a value, W2, depending on quality and use of the web, which is a number equal or less than said consecutive number of data boxes to define a streak;
    b) choosing W1 to define the length of a streak;
    and wherein if said criteria is met, storing a profile location of said streak, wherein said profile location is a location along said machine direction of said streak and along the profile cross direction of said web for use in correction of said actuator to minimize said streak.

* * * * *